Figure 1:
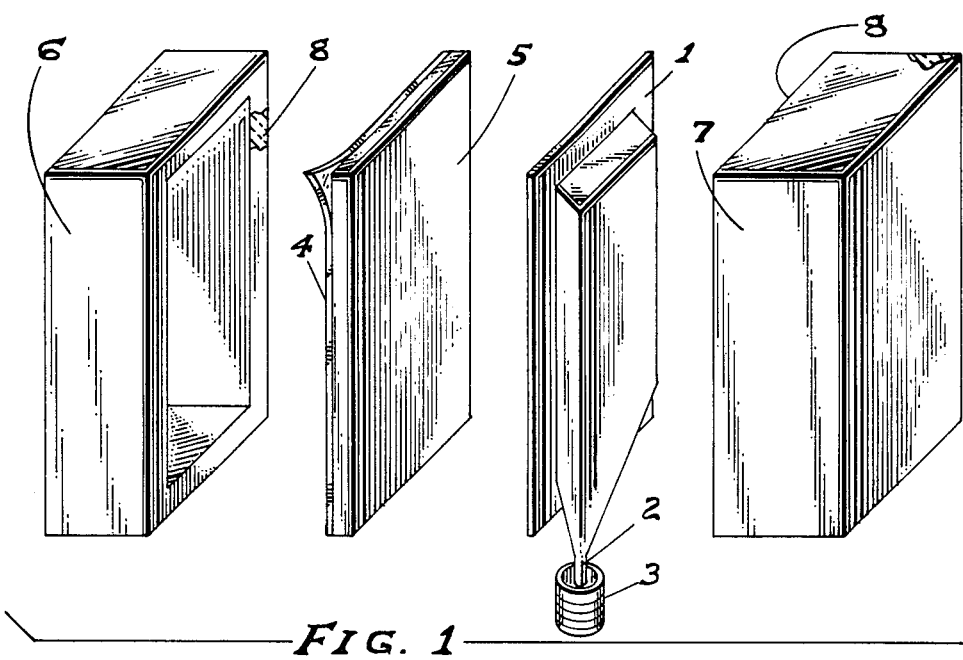

United States Patent [19]

Dumitriu-Valcea et al.

[11] Patent Number: 4,557,138

[45] Date of Patent: Dec. 10, 1985

[54] LARGE-SCALE COLD CUP APPARATUS FOR VAPOR BARRIERS RESISTANCE (PERMEANCE) TESTING

[76] Inventors: Eugene J. Dumitriu-Valcea; Mariana Dumitriu-Valcea, both of 961 Santa Maria Drive, Greenwood, Ind. 46142

[21] Appl. No.: 617,982

[22] Filed: Jun. 6, 1984

[51] Int. Cl.[4] .......................................... G01N 15/08
[52] U.S. Cl. ...................................................... 73/38
[58] Field of Search ............................................ 73/38

[56] References Cited

U.S. PATENT DOCUMENTS

| | | | |
|---|---|---|---|
| 3,286,509 | 11/1966 | Gluckman et al. | 73/38 |
| 3,504,527 | 4/1970 | Marshall | 73/38 |
| 3,590,634 | 7/1971 | Pasternak et al. | 73/38 |
| 4,287,754 | 9/1981 | Heitmann et al. | 73/38 |

FOREIGN PATENT DOCUMENTS

| | | | |
|---|---|---|---|
| 502266 | 6/1976 | U.S.S.R. | 73/38 |
| 617707 | 7/1978 | U.S.S.R. | 73/38 |

*Primary Examiner*—Tim Miles

[57] ABSTRACT

The "large-scale cold cup" testing apparatus covers the large scale vapor barriers permeability resistance (permeance) determination under "temperature and relative humidity nonequilibrium state," at the service conditions, with test values representing "design data", the quantity of vapor permeated through vapor barrier assembly specimen positioned tightly between a "warm" and a "cold" chamber with controlled air temperatures and relative humidities, being measured by means of the quantity of water, originated of the water vapor condensation on the cold side of the vapor barrier assembly and collected into a measuring graduate tightly connected at the bottom of the cold cup.

2 Claims, 11 Drawing Figures

LARGE-SCALE COLD CUP APPARATUS FOR VAPOR BARRIERS RESISTANCE (PERMEANCE) TESTING

BACKGROUND OF THE INVENTION

This invention relates to a "large-scale testing apparatus for water vapor resistance (permeance) determination" of vapor barriers, used in thermal insulation of building envelope systems (e.g. curtain walls, metal buildings, brick and mortar structures, etc.) and in mechanical insulation systems and air handling products (e.g. pipings, ducts and equipment, etc.), in conditions which approximate the service situation. They do provide values that permit the proper vapor barrier design under different conditions of temperature and relative humidity found in service.

The method consists of testing large-scale vapor barrier specimens, installed either on a rigid support plate with known hygro-thermal properties, of different materials (e.g. reinforced concrete, ply board, insulation, etc.), in building envelope systems or directly on the thermal insulation with real thickness in mechanical insulation systems, in function of the vapor barrier type: membrane or mastic and coating and of the using field by means of a "large-scale cold cup," applied on the cold side of the specimen assembly. This cup performs the effect of a "cold surface" upon which vapor condensation occurs.

The water originated of condensation represents the vapor quantity, which passes through the vapor barrier-support assembly.

The specimen and cold cup assembly is positioned tightly between two controlled temperature and relative humidity "warm" and "cold chambers" which conditions approach to the service conditions. All the research and testing institutes are equipped with such controlled atmosphere chambers or with the installations able to realize a controlled atmosphere in special spaces. This method gives the opportunity to test the vapor barriers resistance (permeance) in different interior and exterior service conditions. In this case, the testing values can be considered as "design data."

The conventional vapor permeability test consists of two basic methods: the "dry cup" or "dessicant method" and the "wet cup" or "water method," applied on small-scale specimens. Both methods provide "isothermal conditions" for materials testing. In the "dry cup" or "dessicant method," the relative humidity inside is approximately 0%. In the "wet cup" or "water method," the relative humidity inside is approximately 100%. The dry or wet cups are placed into a controlled test chamber (room or cabinet), with constant temperature and relative humidity. The temperature is between 70° and 90° F. (21° and 32° C.) and shall be maintained constant $+1°$ F. (0.6° C.). The relative humidity is maintained at $50+2\%$, except where extreme of humidity and temperature are desired: $100+1°$ F. ($38+0.6°$ C.) temperature and $90+2\%$ relative humidity. In these circumstances, the vapor barrier resistances obtained by the conventional methods represent very high values, for example of 150... 200 m.$^2$h.mmHg/g for bituminous, rubber, or plastic coatings, of 300... 550 m.$^2$h.mmHg/g for plastic membranes, of 500... 2000 m.$^2$h.mmHg/g for bituminous multilayer roofings and in the case of metal membranes much more higher than these values. These values are much higher than these obtained by the large-scale cold cup method. The explanation is that the conventional methods consider only a few service factors like as the distinction between different materials and the possible defects of materials. These methods cannot be related to the installation defects (especially at joinings) and to the physical-mechanical service loads (temperature and relative humidity differences, moisture, dilations and contractions) of vapor barriers.

That is the reason the conventional methods provide values that permit only the selection and the quality control of vapor barriers materials.

The present invention eliminates the disadvantages of the conventional methods mentioned above because it permits the vapor barrier resistance (permeance) measurement under service conditions of temperature and moisture: "nonequilibrium" (difference) between interior and exterior air temperatures and relative humidities, installation and use conditions. The testing values are in this case real data, which can be used directly in building envelope design.

This invention permits use of the controlled atmosphere chambers supplied by heating, refrigerating and air-conditioning devices, existent in majority of the research and testing institutes.

SUMMARY OF INVENTION

The object of the present invention is to provide a "large-scale vapor barrier permeability testing apparatus," under temperature and moisture service conditions.

It is a further object of the present invention to provide design data for vapor barrier resistance (permeance).

More particularly, according to the present invention, there is provided a "large-scale cold cup," installed tight on the cold side of the vapor barrier assembly sample, which permits evaluating the quantity of the water vapor, diffused through the vapor barrier system. The proceeding is to collect the water, originate of the vapor condensed on the cold cup surface, into a measuring graduated cylinder.

The vapor barrier assembly sample is constituted of a support element, different in function from the barrier type (membrane, coatings) and from the using areas, for example for building envelope systems of minimum 3 feet by 3 feet, limited by the room dimensions. The membrane barriers are installed either included into or applied on the rigid support element surface. The mastics and the coatings are installed on the support element. The assembly is positioned and sealed between two controlled temperature and relative humidity chambers, respectively one "warm" and another "cold," usually existing or easily to be realized in research institutes and testing laboratories.

The characteristics of the controlled chambers atmospheres are, for example in building envelope systems, the following:

| "warm chamber" air | |
|---|---|
| temperature | 50–140° F. (10–60° C.) |
| relative humidity | 40–90% |
| velocity | 0.5–2 mph |
| "cold chamber" air: | |
| temperature | 32–100° F. (0–37.8° C.) |
| relative humidity | 50–90% |
| velocity | 2–15 mph |

For mechanical insulations systems, pipings and ducts, the "large-scale cold cup" has a form adjusted in functions of the pipe's or of the duct's form; it can be in the form of a cylinder for pipes and of a square area tube for ducts.

The "large-scale cold cup" is connected with one or two tubes, through which leaks water, provided from water vapor condensate, into a storage measuring graduated cylinder. This water quantity represents the water vapor quantity, which diffuses through barrier vapor assembly under given interior and exterior air conditions.

The vapor permeability resistance "$R_v$" of the vapor barrier-support element assembly is expressed by the following formula:

$$R_v = \frac{1}{\Lambda_v} = R_{v1} + R_{v2} = \frac{F \cdot \Delta p \cdot \Delta t}{\Delta g} \quad (m^2 \cdot h \cdot Pa/kg); \tag{1}$$

$\Delta g$ = water weight difference between two readings, measured by means of a graduated, transparent cylinder, (kg);

$\Delta p = p_i - p_e$ = vapor pressure difference between the air from both sides of the assembly (vapor barrier and support element) specimen, (Pa);

F = assembly specimen surface, (m$^2$);

$\Delta t$ = period of time between two successive equal vapor permeability (e.g. water quantity) readings, (h);

$\Lambda_v$ = vapor permeance of the assembly specimen, (kg/m.$^2$h.Pa/kg);

$R_{v1}$ = vapor barrier permeability resistance, (m.$^2$h.Pa/kg);

$R_{v2}$ = vapor permeability resistance of the support element plate, (m.$^2$h.Pa/kg).

The vapor permeability resistance of the vapor barrier $R_{v1}$ is given by the expression:

$$R_{v1} = R_v - R_{v2} \ (m.^2h.Pa/kg), \tag{2}$$

$R_{v2}$ = vapor permeability resistance of the support element with known hygro-thermal characteristics, (m.$^2$h.Pa/kg).

If the value $R_{v2}$ is unknown, it can be determined by means of the invention apparatus, in the same conditions as the assembly specimen conditions, without or before the vapor barrier installation. Support elements with high vapor permeability are preferred for a high difference of vapor permeability resistance in comparison with the vapor barriers, i.e. for a higher test accuracy.

The invention apparatus can determine the vapor permeability resistance of samples for temperatures higher than the "dew point," e.g. water vapor diffusion without condensation conditions in any sample section.

This method permits the determination of the vapor barrier resistance for different interior air conditions of relative humidity: 50%, 60%, 70%, 80%, etc., for a given temperature. The test is run in steady state. The proceeding requires to maintain in the initial phase constant interior air parameters: temperature and lowest relative humidity, e.g. 50% until there are reached steady state conditions; after that the relative humidity is increased in steps until the service value, under constant interior temperature conditions.

This method also permits the determination of the vapor barrier resistance for water vapor condensation conditions into the sample; in this case the water collected in the measuring transparent (glass, plastic material) graduate represents the moisture mixture: water+vapor quantity, which passes through the sample.

The "large-scale cold cup" is represented in the following detailed description taken in connection with the accompanying drawings in which:

FIG. 1—is a perspective elevational view of the testing apparatus according to the present invention for building envelope systems.

Figure 2:
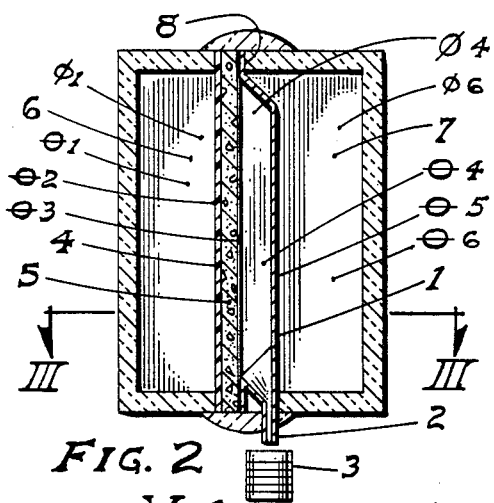

FIG. 2—is a vertical sectional view of the testing apparatus according to the present invention.

Figure 3:
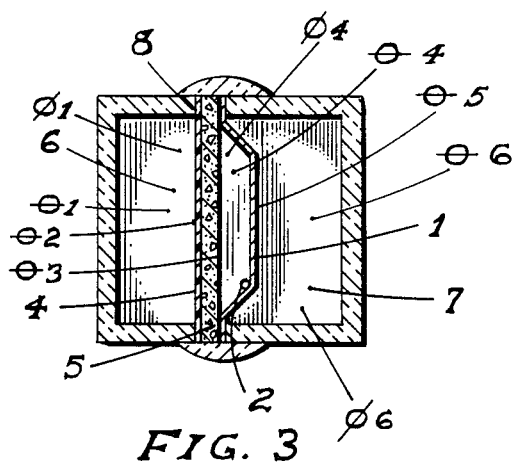

FIG. 3—is a horizontal sectional view taken along the line III—III in FIG. 2.

Figure 4:
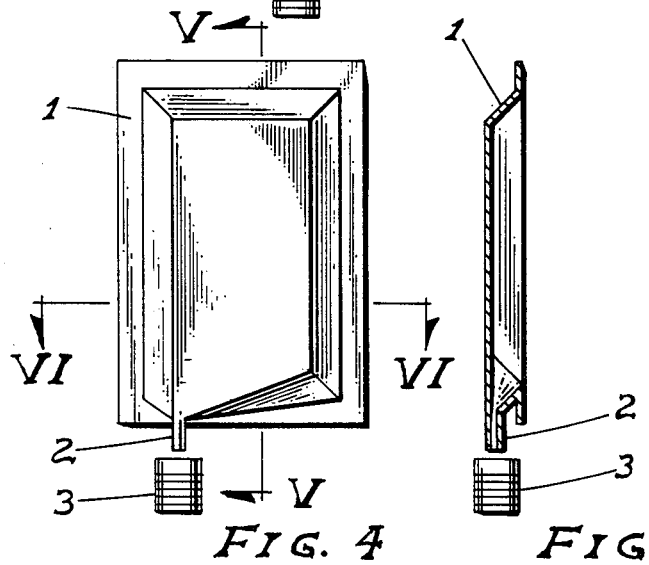

FIG. 4—is a perspective elevational view of the "large-scale cold cup" according to the present invention used for building envelope systems and for plane equipment.

Figure 5:
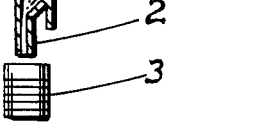

FIG. 5—is a vertical sectional view of the "large-scale cold cup" according to the present invention, taken along with the V—V in FIG. 4.

Figure 6:
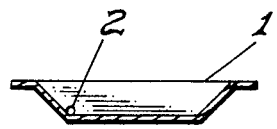

FIG. 6—is a horizontal sectional view taken along the line VI—VI in FIG. 4.

Figure 7A:
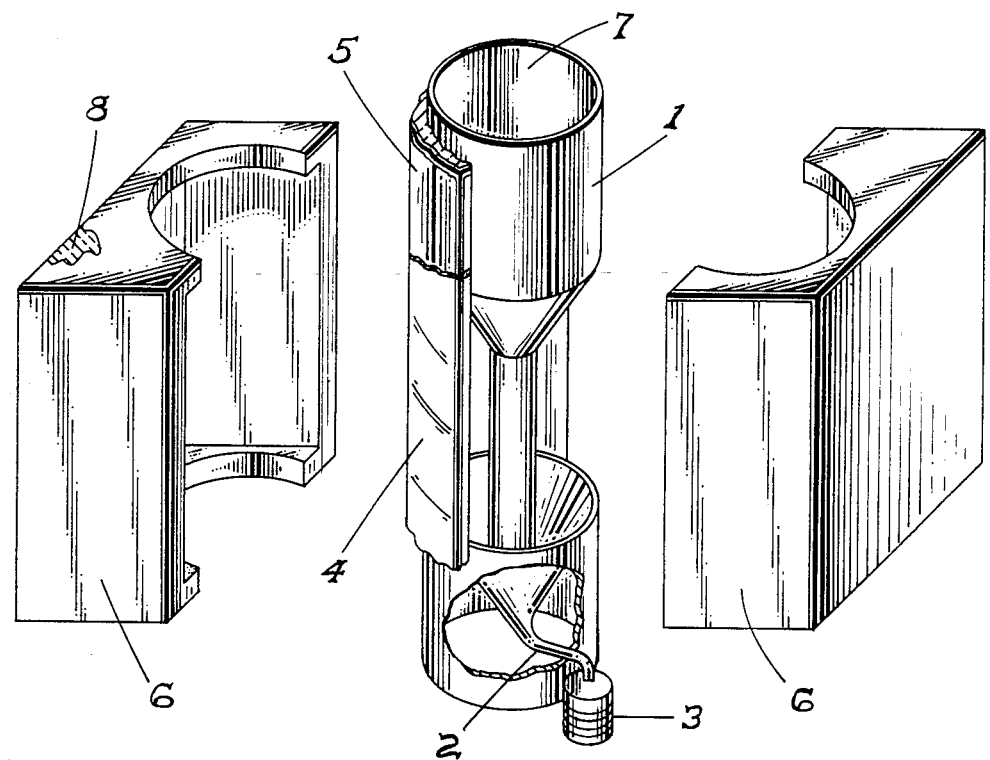
Figure 7B:
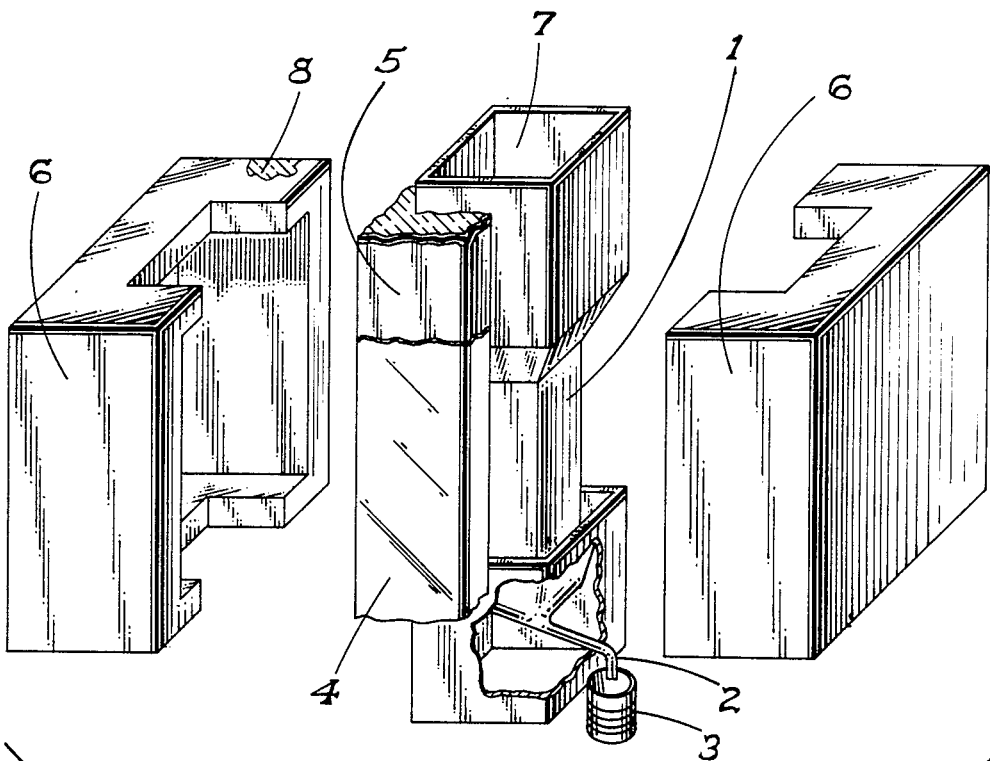

FIG. 7—is a perspective elevational view of the testing apparatus according to the present invention, used for pipings (FIG. 7a) and for ducts (FIG. 7b).

Figure 8:
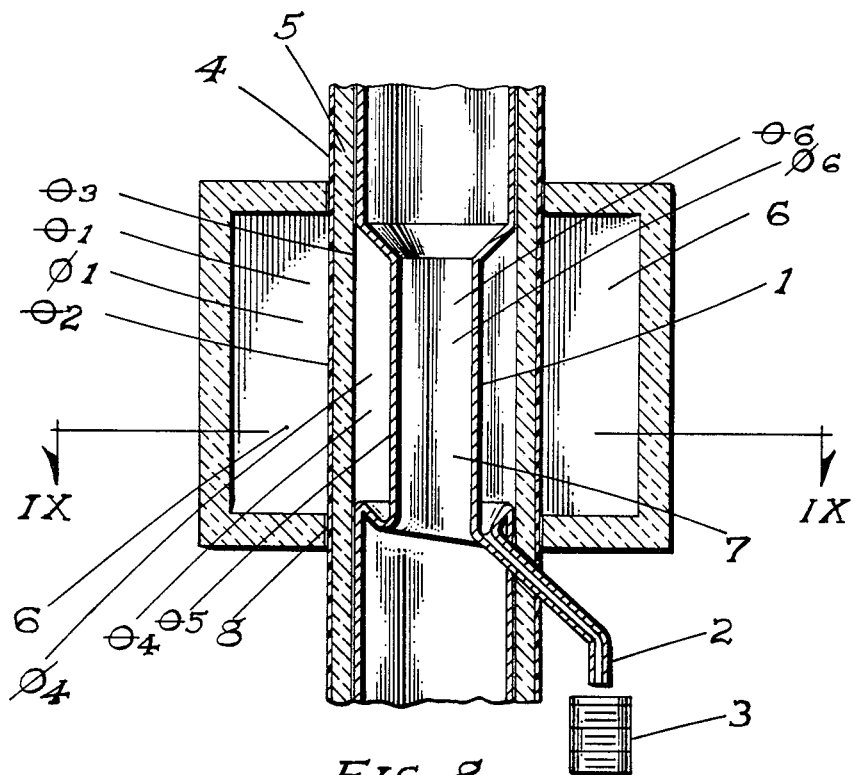

FIG. 8—is a vertical sectional view of the testing apparatus according to the present invention for pipings and for ducts.

Figure 9A:
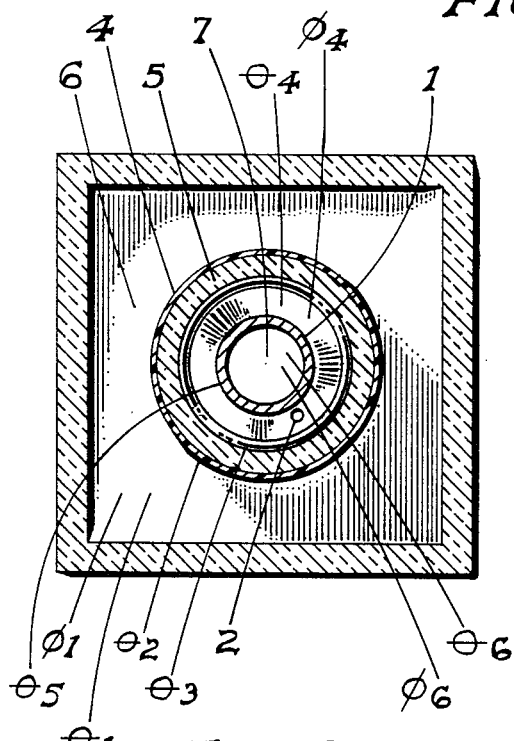
Figure 9B:
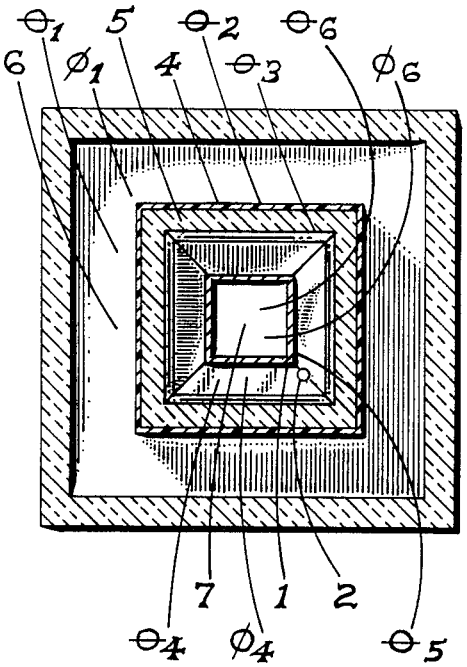

FIG. 9—is a horizontal sectional view taken along the line IX—IX in FIG. 8, for pipings variant (FIG. 9a) and for ducts variant (FIG. 9b).

The preferred embodiment of the apparatus and the method according to the present invention shown in FIG. 1, 2, 3, 4, 5, 6, 7a, 7b, 8, 9a, and 9b, includes a "large-scale cold cup"-1 of a noncorroding metal, of glass or of a transparent (or nontransparent) plastic material with a very smooth interior surface in order to permit a fast down drainage of the water provided from the vapor condensation through the drainage tube-2 into the storage measuring graduated transparent cylinder-3.

The "large-scale cold cup" has the bottom side with a slope of minimum 5% in order to drain the water quickly to the drainage tube (or tubes)-2.

The large-scale assembly: vapor barrier-4 and support element-5 specimen and the "cold cup"-1 are positioned and sealed between two chambers with controlled temperature and relative humidity; a "warm chamber"-6 and another "cold chamber"-7.

The "large-scale cold cup"-1 is tightly connected to the assembly (vapor barrier-4 and support element-5) specimen by means of an adhesive gasket or of a sealant-8 and pressured between the "warm" and "cold" chambers to avoid vapor and air leakage.

The air and the surfaces temperatures of the "large-scale assembly specimen"-4 and 5 and of the "cold cup"-1 are continuously recorded by means of thermocouples, connected with recorders:

$\theta_1$ = air temperature of the "warm chamber"-6, (°K), $\theta_2$ = interior surface temperature of the assembly (vapor barrier-4 and support element-5) specimen, (°K), $\theta_3$ = exterior surface temperature of the assembly specimen-4 and 5, (°K), $\theta_4$ = air temperature of the "cold cup"-1, (°K), $\theta_5$ = surface temperature of the "cold cup"-1, (°K), $\theta_6$ = air temperature of the "cold chamber"-7, (°K), The relative humidity of the air into the "warm" and "cold" chambers and into the "cold cup" is also recorded:

$\phi_1$ = air relative humidity into the "warm chamber,"(%), $\phi_4$ = air relative humidity into the "cold cup (box)," (%), $\phi_6$ = air relative humidity into the "cold chamber," (%).

The vapor pressure of the air and of the vapor barrier assembly can be calculated for specific conditions from psychometric tables showing thermodynamic properties of water saturation.

The advantages of that testing apparatus are the following:

That invention is simple, economical and uses apparatus and equipment for controlled atmosphere chambers, existing in specialized laboratories;

The vapor quantity diffused through the vapor barrier is visible and measured into a graduate;

It is avoided the weighing of the vapor barrier system because it uses the difference between the vapor quantity through the system with and without supporrt element;

It considers the service factors which influence the vapor barrier permeability resistance: factory and installation defects, joining conditions, temperature and relative humidity gradient between the interior and exterior air, air infiltration, etc.;

It determines design values for vapor barrier permeability resistance on statistical testing data basis.

A correct vapor barrier system with exact determined characteristics in service conditions also has a high economical importance. For example, in low temperature industrial constructions with steady state unidirectional vapor flow rate at which water (or ice or both) accumulate into the building envelope depends on the vapor permeability resistance of the vapor barrier system. In this case, the expected life and the operating cost of the low temperature equipment should determine the economic justification for a given insulation installation.

Condensation of migration water vapour within mechanical insulation and building envelope may result in significant damage to systems components and degrade the thermal resistance properties of the insulation. Condensation is a matter that should be considered and quality vapor barriers should be used to reduce the possibility of dangerous condensation.

Vapor barriers will minimize the water vapor diffusion and will increase the effective life of insulation, will conserve energy and reduce energy consumption cost.

The insulation becomes more thermally and economically efficient by the use of adequate design.

We claim as our invention:

1. A "large-scale cold cup testing apparatus" for determination of vapor barriers permeability resistance of permeance in similar conditions as the service conditions especially in relation with temperature and relative humidity gradient, including the combination of:
    a large scale cold cup device for collecting the permeated water vapor flow through vapor barrier systems,
    large-scale specimens of vapor barrier and support plate assembly, realized in real installation conditions, tightly sealed on the cold cup,
    two controlled atmosphere chambers:
        a warm chamber with interior temperature and relative humidity as in real conditions, sealed to the vapor barrier and support plate assembly,
        another cold chamber with exterior air temperature and relative humidity conditions, sealed to the cold cup device,
    air and surface temperature and air relative humidity and material moisture content-measurement devices.

2. A large-scale cold cup device for determination of water vapor flow quantity through vapor barrier systems, according to the claim 1 wherein said large-scale cold cup device comprise a noncorroding smooth metal, glass or transparent (or nontransparent) plastic material cup, positioned tight on the cold side of the vapor barrier assembly specimen and connected tight at the bottom with a collector measuring graduated glass or transparent plastic material cylinder, the water flowing into representing the water vapor quantity diffused through vapor barrier assembly and condensated on the interior surface of the cold cup.

* * * * *